(12) United States Patent
Anderson et al.

(10) Patent No.: US 8,262,698 B2
(45) Date of Patent: Sep. 11, 2012

(54) EXPANDABLE DEVICE FOR INSERTION BETWEEN ANATOMICAL STRUCTURES AND A PROCEDURE UTILIZING SAME

(75) Inventors: Kent M. Anderson, Memphis, TN (US); Eric C. Lange, Collierville, TN (US); Hai H. Trieu, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 964 days.

(21) Appl. No.: 11/376,991

(22) Filed: Mar. 16, 2006

(65) Prior Publication Data

US 2007/0233074 A1    Oct. 4, 2007

(51) Int. Cl.
*A61B 17/70* (2006.01)

(52) U.S. Cl. .................. 606/249; 606/248

(58) Field of Classification Search .......... 606/61, 606/90, 248–249; 623/17.11–17.16
See application file for complete search history.

(56) References Cited

U.S. PATENT DOCUMENTS

| | | | |
|---|---|---|---|
| 624,969 A | 5/1899 | Peterson | |
| 1,153,797 A | 9/1915 | Kegreisz | |
| 1,516,347 A | 11/1924 | Pataky | |
| 1,870,942 A | 8/1932 | Beatty | |
| 2,077,804 A | 4/1937 | Morrison | |
| 2,299,308 A | 10/1942 | Creighton | |
| 2,485,531 A | 10/1949 | Dzus et al. | |
| 2,607,370 A | 8/1952 | Anderson | |
| 2,677,369 A | 5/1954 | Knowles | |
| 2,685,877 A | 8/1954 | Dobelle | |
| 3,065,659 A | 11/1962 | Eriksson et al. | |
| 3,108,595 A | 10/1963 | Overment | |
| 3,397,699 A | 8/1968 | Kohl | |
| 3,426,364 A | 2/1969 | Lumb | |
| 3,648,691 A | 3/1972 | Lumb et al. | |
| 3,779,239 A | 12/1973 | Fischer et al. | |
| 4,011,602 A | 3/1977 | Rybicki et al. | |
| 4,237,875 A | 12/1980 | Termanini | |
| 4,257,409 A | 3/1981 | Bacal et al. | |
| 4,274,324 A | 6/1981 | Giannuzzi | |
| 4,289,123 A | 9/1981 | Dunn | |
| 4,327,736 A | 5/1982 | Inoue | |

(Continued)

FOREIGN PATENT DOCUMENTS

DE    2821678 A1    11/1979

(Continued)

OTHER PUBLICATIONS

U.S. Appl. No. 11/359,070, filed Feb. 22, 2006, Bruneau. et al.

(Continued)

*Primary Examiner* — Thomas Barrett
*Assistant Examiner* — Matthew Lawson

(57) ABSTRACT

An interspinous implant includes a spacer having an upwardly facing concave saddle and a downwardly facing concave saddle. The lateral sides of the implant are pulled inward to force the saddles vertically away from each other, thereby increasing the effective height of the implant. In one version, a strap extends circumferentially around the anterior and posterior surfaces of the spacer, such that tightening the strap causes the saddles to move away from each other. In another version, the spacer includes a first outwardly facing convex segment disposed on a first lateral side of the saddles and a second outwardly facing convex segment disposed on a second lateral side of the saddles. A rod extends between the first and second convex segments and is fixed to the first convex segment and movable relative to the second convex segment.

8 Claims, 5 Drawing Sheets

U.S. PATENT DOCUMENTS

| | | |
|---|---|---|
| 4,401,112 A | 8/1983 | Rezaian |
| 4,499,636 A | 2/1985 | Tanaka |
| 4,519,100 A | 5/1985 | Wills et al. |
| 4,553,273 A | 11/1985 | Wu |
| 4,554,914 A | 11/1985 | Kapp et al. |
| 4,573,454 A | 3/1986 | Hoffman |
| 4,592,341 A | 6/1986 | Omagari et al. |
| 4,599,086 A | 7/1986 | Doty |
| 4,604,995 A | 8/1986 | Stephens et al. |
| 4,611,582 A | 9/1986 | Duff |
| 4,632,101 A | 12/1986 | Freedland |
| 4,636,217 A | 1/1987 | Ogilvie et al. |
| 4,646,998 A | 3/1987 | Pate |
| 4,657,550 A | 4/1987 | Daher |
| 4,662,808 A | 5/1987 | Camilleri |
| 4,686,970 A | 8/1987 | Dove et al. |
| 4,704,057 A | 11/1987 | McSherry |
| 4,721,103 A | 1/1988 | Freedland |
| 4,759,769 A | 7/1988 | Hedman et al. |
| 4,787,378 A | 11/1988 | Sodhi |
| 4,822,226 A | 4/1989 | Kennedy |
| 4,827,918 A | 5/1989 | Olerud |
| 4,834,600 A | 5/1989 | Lemke |
| 4,863,476 A | 9/1989 | Shepperd |
| 4,886,405 A | 12/1989 | Blomberg |
| 4,892,545 A | 1/1990 | Day et al. |
| 4,913,144 A | 4/1990 | Del Medico |
| 4,931,055 A | 6/1990 | Bumpus et al. |
| 4,932,975 A | 6/1990 | Main et al. |
| 4,969,887 A | 11/1990 | Sodhi |
| 5,000,166 A | 3/1991 | Karpf |
| 5,011,484 A * | 4/1991 | Breard .......................... 606/249 |
| 5,047,055 A | 9/1991 | Bao et al. |
| 5,059,193 A | 10/1991 | Kuslich |
| 5,092,866 A | 3/1992 | Breard et al. |
| 5,098,433 A | 3/1992 | Freedland |
| 5,171,278 A | 12/1992 | Pisharodi |
| 5,201,734 A | 4/1993 | Cozad et al. |
| 5,267,999 A | 12/1993 | Olerud |
| 5,290,312 A | 3/1994 | Kojimoto et al. |
| 5,306,275 A | 4/1994 | Bryan |
| 5,306,310 A | 4/1994 | Siebels |
| 5,312,405 A | 5/1994 | Korotko et al. |
| 5,316,422 A | 5/1994 | Coffman |
| 5,356,423 A | 10/1994 | Tihon et al. |
| 5,360,430 A | 11/1994 | Lin |
| 5,366,455 A | 11/1994 | Dove et al. |
| 5,370,697 A | 12/1994 | Baumgartner |
| 5,390,638 A * | 2/1995 | Hornby et al. ................ 123/456 |
| 5,390,683 A | 2/1995 | Pisharodi |
| 5,395,370 A | 3/1995 | Muller et al. |
| 5,401,269 A | 3/1995 | Buttner-Janz et al. |
| 5,403,316 A | 4/1995 | Ashman |
| 5,415,661 A | 5/1995 | Holmes |
| 5,437,672 A | 8/1995 | Alleyne |
| 5,437,674 A | 8/1995 | Worcel et al. |
| 5,439,463 A | 8/1995 | Lin |
| 5,454,812 A | 10/1995 | Lin |
| 5,456,689 A | 10/1995 | Kresch et al. |
| 5,458,641 A | 10/1995 | Ramirez Jimenez |
| 5,480,442 A | 1/1996 | Bertagnoli |
| 5,496,318 A | 3/1996 | Howland et al. |
| 5,518,498 A | 5/1996 | Lindenberg et al. |
| 5,554,191 A | 9/1996 | Lahille et al. |
| 5,562,662 A | 10/1996 | Brumfield et al. |
| 5,562,735 A | 10/1996 | Margulies |
| 5,571,192 A | 11/1996 | Schonhoffer |
| 5,609,634 A | 3/1997 | Voydeville |
| 5,609,635 A | 3/1997 | Michelson |
| 5,628,756 A | 5/1997 | Barker, Jr. et al. |
| 5,630,816 A | 5/1997 | Kambin |
| 5,645,599 A | 7/1997 | Samani |
| 5,653,762 A | 8/1997 | Pisharodi |
| 5,653,763 A | 8/1997 | Errico et al. |
| 5,658,335 A | 8/1997 | Allen |
| 5,665,122 A | 9/1997 | Kambin |
| 5,674,295 A | 10/1997 | Ray et al. |
| 5,676,702 A | 10/1997 | Ratron |
| 5,685,826 A | 11/1997 | Bonutti |
| 5,690,649 A | 11/1997 | Li |
| 5,693,100 A | 12/1997 | Pisharodi |
| 5,702,395 A | 12/1997 | Hopf |
| 5,702,452 A | 12/1997 | Argenson et al. |
| 5,702,455 A | 12/1997 | Saggar |
| 5,707,390 A | 1/1998 | Bonutti |
| 5,716,416 A | 2/1998 | Lin |
| 5,723,013 A | 3/1998 | Jeanson et al. |
| 5,725,341 A | 3/1998 | Hofmeister |
| 5,746,762 A | 5/1998 | Bass |
| 5,755,797 A | 5/1998 | Baumgartner |
| 5,800,547 A | 9/1998 | Schafer et al. |
| 5,810,815 A | 9/1998 | Morales |
| 5,836,948 A | 11/1998 | Zucherman et al. |
| 5,849,004 A | 12/1998 | Bramlet |
| 5,860,977 A | 1/1999 | Zucherman et al. |
| 5,888,196 A | 3/1999 | Bonutti |
| 5,941,881 A | 8/1999 | Barnes |
| 5,976,186 A | 11/1999 | Bao et al. |
| 5,980,523 A | 11/1999 | Jackson |
| 6,022,376 A | 2/2000 | Assell et al. |
| 6,048,342 A | 4/2000 | Zucherman et al. |
| 6,059,829 A | 5/2000 | Schlapfer et al. |
| 6,068,630 A | 5/2000 | Zucherman et al. |
| 6,074,390 A | 6/2000 | Zucherman et al. |
| 6,102,922 A | 8/2000 | Jakobsson et al. |
| 6,113,638 A | 9/2000 | Williams et al. |
| 6,126,689 A | 10/2000 | Brett |
| 6,126,691 A | 10/2000 | Kasra et al. |
| 6,127,597 A | 10/2000 | Beyar et al. |
| 6,132,464 A | 10/2000 | Martin |
| 6,143,031 A | 11/2000 | Knothe et al. |
| 6,190,413 B1 | 2/2001 | Sutcliffe |
| 6,190,414 B1 | 2/2001 | Young |
| 6,214,037 B1 | 4/2001 | Mitchell et al. |
| 6,214,050 B1 | 4/2001 | Huene |
| 6,224,631 B1 | 5/2001 | Kohrs |
| 6,245,107 B1 | 6/2001 | Ferree |
| 6,293,949 B1 | 9/2001 | Justis et al. |
| 6,325,827 B1 | 12/2001 | Lin |
| 6,336,930 B1 | 1/2002 | Stalcup et al. |
| 6,348,053 B1 | 2/2002 | Cachia |
| 6,352,537 B1 | 3/2002 | Strnad |
| 6,364,883 B1 | 4/2002 | Santilli |
| 6,371,987 B1 | 4/2002 | Weiland et al. |
| 6,375,682 B1 | 4/2002 | Fleischmann et al. |
| 6,383,221 B1 | 5/2002 | Scarborough et al. |
| 6,402,750 B1 | 6/2002 | Atkinson et al. |
| 6,402,751 B1 | 6/2002 | Hoeck et al. |
| 6,419,703 B1 | 7/2002 | Fallin et al. |
| 6,419,704 B1 | 7/2002 | Ferree |
| 6,432,130 B1 | 8/2002 | Hanson |
| 6,440,169 B1 | 8/2002 | Elberg et al. |
| 6,447,513 B1 | 9/2002 | Griggs |
| 6,451,019 B1 | 9/2002 | Zucherman et al. |
| 6,500,178 B2 | 12/2002 | Zucherman et al. |
| 6,511,508 B1 * | 1/2003 | Shahinpoor et al. ........... 623/4.1 |
| 6,514,256 B2 | 2/2003 | Zucherman et al. |
| 6,520,991 B2 | 2/2003 | Huene |
| 6,554,833 B2 | 4/2003 | Levy |
| 6,582,433 B2 | 6/2003 | Yun |
| 6,582,467 B1 | 6/2003 | Teitelbaum et al. |
| 6,592,585 B2 | 7/2003 | Choi et al. |
| 6,626,944 B1 * | 9/2003 | Taylor ........................ 623/17.16 |
| 6,626,994 B1 * | 9/2003 | Kimura et al. .................. 117/84 |
| 6,645,207 B2 | 11/2003 | Dixon et al. |
| 6,669,729 B2 | 12/2003 | Chin |
| 6,685,742 B1 | 2/2004 | Jackson |
| 6,695,842 B2 | 2/2004 | Zucherman et al. |
| 6,699,246 B2 | 3/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,531 B1 | 5/2004 | Trieu |
| 6,733,534 B2 | 5/2004 | Sherman |
| 6,736,818 B2 | 5/2004 | Perren et al. |
| 6,743,257 B2 | 6/2004 | Castro |
| 6,758,863 B2 | 7/2004 | Estes et al. |

| Patent/Publication | Date | Inventor(s) |
|---|---|---|
| 6,761,720 B1 | 7/2004 | Senegas |
| 6,770,096 B2 | 8/2004 | Bolger et al. |
| 6,783,530 B1 | 8/2004 | Levy |
| 6,835,205 B2 | 12/2004 | Atkinson et al. |
| 6,902,580 B2 | 6/2005 | Fallin et al. |
| 6,905,512 B2 | 6/2005 | Paes et al. |
| 6,946,000 B2 | 9/2005 | Senegas et al. |
| 6,981,975 B2 | 1/2006 | Michelson |
| 7,011,685 B2 | 3/2006 | Arnin et al. |
| 7,041,136 B2 | 5/2006 | Goble et al. |
| 7,048,736 B2 | 5/2006 | Robinson et al. |
| 7,070,598 B2 | 7/2006 | Lim et al. |
| 7,081,120 B2 | 7/2006 | Li et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,097,654 B1 | 8/2006 | Freedland |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,431,735 B2 | 10/2008 | Liu et al. |
| 7,442,208 B2 | 10/2008 | Mathieu et al. |
| 7,445,637 B2 * | 11/2008 | Taylor .................. 623/17.16 |
| 7,458,981 B2 | 12/2008 | Fielding et al. |
| 7,524,324 B2 * | 4/2009 | Winslow et al. .............. 606/248 |
| 7,582,106 B2 | 9/2009 | Teitelbaum et al. |
| 7,604,652 B2 | 10/2009 | Arnin et al. |
| 7,611,316 B2 | 11/2009 | Panasik et al. |
| 7,621,950 B1 | 11/2009 | Globerman et al. |
| 7,658,752 B2 | 2/2010 | Labrom et al. |
| 7,749,252 B2 | 7/2010 | Zucherman et al. |
| 7,771,456 B2 | 8/2010 | Hartmann et al. |
| 7,862,615 B2 | 1/2011 | Carli et al. |
| 7,901,430 B2 | 3/2011 | Matsuura et al. |
| 2001/0016743 A1 | 8/2001 | Zucherman et al. |
| 2002/0143331 A1 | 10/2002 | Zucherman et al. |
| 2003/0040746 A1 | 2/2003 | Mitchell et al. |
| 2003/0045940 A1 | 3/2003 | Eberlein et al. |
| 2003/0065330 A1 | 4/2003 | Zucherman et al. |
| 2003/0153915 A1 | 8/2003 | Nekozuka et al. |
| 2004/0010312 A1 | 1/2004 | Enayati |
| 2004/0010316 A1 | 1/2004 | William et al. |
| 2004/0087947 A1 | 5/2004 | Lim et al. |
| 2004/0097931 A1 | 5/2004 | Mitchell |
| 2004/0106995 A1 | 6/2004 | LeCouedic et al. |
| 2004/0117017 A1 | 6/2004 | Pasquet et al. |
| 2004/0133204 A1 | 7/2004 | Davies |
| 2004/0133280 A1 | 7/2004 | Trieu |
| 2004/0158248 A1 | 8/2004 | Ginn |
| 2004/0167625 A1 | 8/2004 | Beyar et al. |
| 2004/0199255 A1 * | 10/2004 | Mathieu et al. .............. 623/17.11 |
| 2004/0260397 A1 | 12/2004 | Lambrecht et al. |
| 2005/0010293 A1 | 1/2005 | Zucherman et al. |
| 2005/0033434 A1 | 2/2005 | Berry |
| 2005/0049708 A1 | 3/2005 | Atkinson et al. |
| 2005/0085814 A1 | 4/2005 | Sherman et al. |
| 2005/0143827 A1 | 6/2005 | Globerman et al. |
| 2005/0165398 A1 | 7/2005 | Reiley |
| 2005/0203512 A1 | 9/2005 | Hawkins et al. |
| 2005/0203519 A1 | 9/2005 | Harms et al. |
| 2005/0203624 A1 | 9/2005 | Serhan et al. |
| 2005/0228391 A1 | 10/2005 | Levy et al. |
| 2005/0245937 A1 | 11/2005 | Winslow |
| 2005/0261768 A1 * | 11/2005 | Trieu .................. 623/17.11 |
| 2005/0267579 A1 | 12/2005 | Reiley et al. |
| 2005/0273166 A1 | 12/2005 | Sweeney |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0064165 A1 | 3/2006 | Zucherman et al. |
| 2006/0084983 A1 | 4/2006 | Kim |
| 2006/0084985 A1 * | 4/2006 | Kim .................. 606/61 |
| 2006/0084987 A1 | 4/2006 | Kim |
| 2006/0084988 A1 | 4/2006 | Kim |
| 2006/0085069 A1 | 4/2006 | Kim |
| 2006/0085070 A1 * | 4/2006 | Kim .................. 623/17.11 |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0129239 A1 | 6/2006 | Kwak |
| 2006/0136060 A1 * | 6/2006 | Taylor .................. 623/17.13 |
| 2006/0142858 A1 | 6/2006 | Colleran et al. |
| 2006/0149242 A1 | 7/2006 | Kraus et al. |
| 2006/0182515 A1 | 8/2006 | Panasik et al. |
| 2006/0184247 A1 * | 8/2006 | Edidin et al. .............. 623/17.11 |
| 2006/0184248 A1 | 8/2006 | Edidin et al. |
| 2006/0195102 A1 | 8/2006 | Malandain |
| 2006/0217726 A1 * | 9/2006 | Maxy et al. .................. 606/72 |
| 2006/0224159 A1 | 10/2006 | Anderson |
| 2006/0224241 A1 | 10/2006 | Butler et al. |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241613 A1 | 10/2006 | Bruneau et al. |
| 2006/0241643 A1 | 10/2006 | Lim et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0271044 A1 | 11/2006 | Petrini et al. |
| 2006/0271049 A1 | 11/2006 | Zucherman et al. |
| 2006/0271061 A1 | 11/2006 | Beyar et al. |
| 2006/0276790 A1 * | 12/2006 | Dawson et al. .............. 606/61 |
| 2006/0282075 A1 | 12/2006 | Labrom et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0010813 A1 | 1/2007 | Zucherman et al. |
| 2007/0032790 A1 | 2/2007 | Aschmann et al. |
| 2007/0043362 A1 | 2/2007 | Malandain et al. |
| 2007/0043363 A1 | 2/2007 | Malandain et al. |
| 2007/0073289 A1 | 3/2007 | Kwak et al. |
| 2007/0100340 A1 | 5/2007 | Lange et al. |
| 2007/0123861 A1 | 5/2007 | Dewey et al. |
| 2007/0142915 A1 | 6/2007 | Altarac et al. |
| 2007/0151116 A1 | 7/2007 | Malandain |
| 2007/0162000 A1 | 7/2007 | Perkins |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0191838 A1 * | 8/2007 | Bruneau et al. .............. 606/61 |
| 2007/0198091 A1 | 8/2007 | Boyer et al. |
| 2007/0225807 A1 | 9/2007 | Phan et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276493 A1 | 11/2007 | Malandain et al. |

| | | | |
|---|---|---|---|
| 2007/0276496 A1 | 11/2007 | Lange et al. | |
| 2007/0276497 A1 | 11/2007 | Anderson | |
| 2007/0282443 A1 | 12/2007 | Globerman et al. | |
| 2008/0021457 A1 | 1/2008 | Anderson et al. | |
| 2008/0021460 A1 | 1/2008 | Bruneau et al. | |
| 2008/0058934 A1 | 3/2008 | Malandain et al. | |
| 2008/0097446 A1 | 4/2008 | Reiley et al. | |
| 2008/0114357 A1 | 5/2008 | Allard et al. | |
| 2008/0114358 A1 | 5/2008 | Anderson et al. | |
| 2008/0114456 A1 | 5/2008 | Dewey et al. | |
| 2008/0147190 A1 | 6/2008 | Dewey et al. | |
| 2008/0161818 A1 | 7/2008 | Kloss et al. | |
| 2008/0167685 A1 | 7/2008 | Allard et al. | |
| 2008/0183209 A1 | 7/2008 | Robinson et al. | |
| 2008/0183211 A1 | 7/2008 | Lamborne et al. | |
| 2008/0183218 A1 | 7/2008 | Mueller et al. | |
| 2008/0195152 A1 | 8/2008 | Altarac et al. | |
| 2008/0215094 A1 | 9/2008 | Taylor | |
| 2008/0221685 A9 | 9/2008 | Altarac et al. | |
| 2008/0234824 A1 | 9/2008 | Youssef et al. | |
| 2008/0262617 A1 | 10/2008 | Froehlich et al. | |
| 2008/0281360 A1 | 11/2008 | Vittur et al. | |
| 2008/0281361 A1 | 11/2008 | Vittur et al. | |
| 2009/0062915 A1 | 3/2009 | Kohm et al. | |
| 2009/0105766 A1 | 4/2009 | Thompson et al. | |
| 2009/0105773 A1 | 4/2009 | Lange et al. | |
| 2009/0234389 A1 | 9/2009 | Chuang et al. | |
| 2009/0240283 A1 | 9/2009 | Carls et al. | |
| 2009/0270918 A1 | 10/2009 | Attia et al. | |
| 2010/0121379 A1 | 5/2010 | Edmond | |
| 2010/0204732 A1 | 8/2010 | Aschmann et al. | |

FOREIGN PATENT DOCUMENTS

| | | |
|---|---|---|
| DE | 3922044 A1 | 2/1991 |
| DE | 4012622 C1 | 7/1991 |
| EP | 0322334 B1 | 2/1992 |
| EP | 0767636 B1 | 1/1999 |
| EP | 1004276 A1 | 5/2000 |
| EP | 1011464 B1 | 6/2000 |
| EP | 1138268 A1 | 10/2001 |
| EP | 1148850 B1 | 10/2001 |
| EP | 1148851 B1 | 10/2001 |
| EP | 1302169 A1 | 4/2003 |
| EP | 1330987 A1 | 7/2003 |
| EP | 1152797 A2 | 7/2005 |
| EP | 1854433 A1 | 11/2007 |
| EP | 1905392 A1 | 4/2008 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2717675 A1 | 3/1994 |
| FR | 2700941 A1 | 8/1994 |
| FR | 2703239 A1 | 10/1994 |
| FR | 2707864 A1 | 1/1995 |
| FR | 2730156 A1 | 2/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2774581 A1 | 8/1999 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| JP | 2003079649 | 3/2003 |
| SU | 988281 | 1/1983 |
| SU | 1484348 A1 | 6/1989 |
| SU | 1484348 | 7/1989 |
| WO | WO 94/26192 | 11/1994 |
| WO | WO 94/26195 | 11/1994 |
| WO | WO 97/18769 | 5/1997 |
| WO | WO 98/20939 | 5/1998 |
| WO | WO 99/26562 | 6/1999 |
| WO | WO 00/44319 | 8/2000 |
| WO | WO 01/54598 A1 | 8/2001 |
| WO | WO 03/057055 A1 | 7/2003 |
| WO | WO 2004/047689 A1 | 6/2004 |
| WO | WO 2004/047691 A1 | 6/2004 |
| WO | WO 2004/084743 A1 | 10/2004 |
| WO | WO 2004/084768 A2 | 10/2004 |
| WO | WO 2004/110300 A2 | 12/2004 |
| WO | 2005/009300 | 2/2005 |
| WO | WO 2005/009300 A1 | 2/2005 |
| WO | WO 2005/011507 A1 | 2/2005 |
| WO | WO 2005/044118 A1 | 5/2005 |
| WO | WO 2005/048856 A1 | 6/2005 |
| WO | WO 2005/110258 A1 | 11/2005 |
| WO | WO 2006/064356 A1 | 6/2006 |
| WO | WO 2007/034516 A1 | 3/2007 |
| WO | WO 2007/052975 A1 | 5/2007 |
| WO | WO2007052975 A | 5/2007 |
| WO | 2007119157 A1 | 10/2007 |
| WO | WO 2009/083276 A1 | 7/2009 |
| WO | WO 2009/083583 A1 | 7/2009 |
| WO | WO 2009/098536 A1 | 8/2009 |

OTHER PUBLICATIONS

U.S. Appl. No. 11/333,919, filed Jan. 18, 2006, Dewey, et al.
U.S. Appl. No. 11/334,691, filed Jan. 18, 2006, Lange, et al.
U.S. Appl. No. 11/271,018, filed Nov. 10, 2005, Dewey, et al.
U.S. Appl. No. 11/261,386, filed Oct. 27, 2005, Lange, et al.
U.S. Appl. No. 11/67,775, filed Jun. 27, 2005, Anderson, et al.
U.S. Appl. No. 11/095,215, filed Mar. 31, 2005, Anderson.
U.S. Appl. No. 11/095,214, filed Mar. 31, 2005, Anderson.
European Patent Office, International Searching Authority, Notification of Transmittal of the International Search Report and the Written Opinion of the International Searching Authority or the Declaration, International Application No. PCT/US2007/063281, Jul. 31, 2007, 13 pages.
European Patent Office, International Searching Authority, Notification of Transmittal of the International Search Report and the Written Opinion of the International Searching Authority or the Declaration, International Application No. PCT/US2007/062405, Aug. 2, 2007, 9 pages.
"Dispositivo Intervertebrale Ammortizzante DIAM," date unknown, p. 1.
"Tecnica Operatoria Per II Posizionamento Della Protesi DIAM," date unknown, pp. 1-3.
"Wallis Operative Technique: Surgical Procedure for Treatment of Degenerative Disc Disease (DDD) of Lumbar Spine," date unknown, pp. 1-24, Spine Next, an Abbott Laboratories company, Bordeaux, France.
Benzel et al., "Posterior Cervical Interspinous Compression Wiring and Fusion for Mid to Low Cervical Spinal Injuries," J. Neurosurg., Jun. 1989, pp. 893-899, vol. 70.
Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.
Christie et al., "Dynamic Interspinous Process Technology," SPINE, 2005, pp. S73-S78, vol. 30, No. 16S.
Cousin Biotech, "Analysis of Clinical Experience with a Posterior Shock-Absorbing Implant," date unknown, pp. 2-9.
Cousin Biotech, Dispositif Intervertébral Amortissant, Jun. 1998, pp. 1-4.
Cousin Biotech, Technique Operatoire de la Prothese DIAM, date unknown, Annexe 1, pp. 1-8.
Dickman et al., "The Interspinous Method of Posterior Atlantoaxial Arthrodesis," J. Neurosurg., Feb. 1991, pp. 190-198, vol. 74.
Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.
Ebara et al., "Inoperative Measurement of Lumbar Spinal Instability," SPINE, 1992, pp. S44-S50, vol. 17, No. 3S.
Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Scarfò, "Instability/Stenosis: Holistic Approach for Less Invasive Surgery," date unknown, University of Siena, Siena, Italy.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sté noses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodèse," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Sulzer Innotec, "Diam—Modified CAD Geometry and Meshing," date unknown.

Taylor et al., "Analyse d'une expérience clinique d'un implant postérieur amortissant," Rachis Revue de Pathologie Vertébrate, Oct./Nov. 1999, vol. 11, No. 4-5, Gieda Inter Rachis.

Taylor et al., "Surgical Requirement for the Posterior Control of the Rotational Centers," date unknown.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Posterior Dynamic Stabilization using the DIAM (Device for Intervertebral Assisted Motion)," date unknown, pp. 1-5.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zucherman et al., "Clinical Efficacy of Spinal Instrumentation in Lumbar Degenerative Disc Disease," SPINE, Jul. 1992, pp. 834-837, vol. 17, No. 7.

Anasetti et al., "Spine Stability After Implantation of an Interspinous Device: An In Vitro and Finite Element Biomechanical Study," J. Neurosurg. Spine, Nov. 2010, vol. 13, pp. 568-575.

Bellini et al., "Biomechanics of the Lumbar Spine Afer Dynamic Stabilization," J. Spinal Discord Tech., 2006, vol. 00, No. 00, pp. 1-7.

Buric et al., "DIAM Device for Low Back Pain in Degenerative Disc Disease 24 Months Follow-up," Advances in Minimally Invasive Surgery and Therapy for Spine and Nerves, Alexandre et al., eds., 2011, pp. 177-182, Spinger-Verlat/Wien.

Phillips et al., "Biomechanics of Posterior Dynamic Stabiling Device (DIAM) After Facetectomy and Disectomy," The Spine Journal, 2006, vol. 6, pp. 714-722.

Taylor et al., "Device for Intervertebral Assisted Motion: Technique and Intial Results," 22 Neurosurg. Focus, Jan. 2007, vol. 22, No. 1, pp. 1-6.

Wilke et al., "Biomedical Effect of Different Lumbar Interspinous Implants on Flexibilty and Intradiscal Pressure," Eur Spine J., Vo. 17, published online Jun. 27, 2008, pp. 1049-1056.

Zhao et al., "Efficacy of the Dynamic Interspinous Assisted Motion System in Clinical Treatment of Degenerative Lumbar Disease," Chin. Med. J., 2010, vol. 123, No. 21, pp. 2974-2977.

Kramer et al., "Intervetertebral Disk Diseases: Causes, Diagnosis, Treatment and Prophylaxis," pp. 244-249, Medical, 1990.

Zdeblick et al., "Two-Point Fixation of the Lumbar Spine Differential Stability in Rotation," SPINE, 1991, pp. S298-S301, vol. 16, No. 6, Supplement.

\* cited by examiner

US 8,262,698 B2

EXPANDABLE DEVICE FOR INSERTION BETWEEN ANATOMICAL STRUCTURES AND A PROCEDURE UTILIZING SAME

BACKGROUND

The present invention relates to an expandable device for insertion between anatomical structures and a procedure utilizing same.

It is often desirable to insert a device between anatomical structures for several reasons. For example, it can be inserted between two structures in a manner so that it engages the structures and serves as an implant for stabilizing the structures and absorbing shock. Alternately, a device can be temporarily inserted between the structures and function to distract the structures to permit another device, such as a prosthesis, to be implanted between the structures. According to another example, a device can be inserted between the structures and distract the structures to permit another surgical procedure to be performed in the space formed by the distraction, after which the device is released and removed.

Although devices have been designed for one or more of the above uses they are not without problems. For example, it is often difficult to insert the device without requiring excessive invasion of the anatomy, damage to the adjacent anatomical structures, or over-distraction. Embodiments of the present invention improve upon these techniques, and various embodiments of the invention may possess one or more of the above features and advantages, or provide one or more solutions to the above problems existing in the prior art.

DETAILED DESCRIPTION

Figure 1:
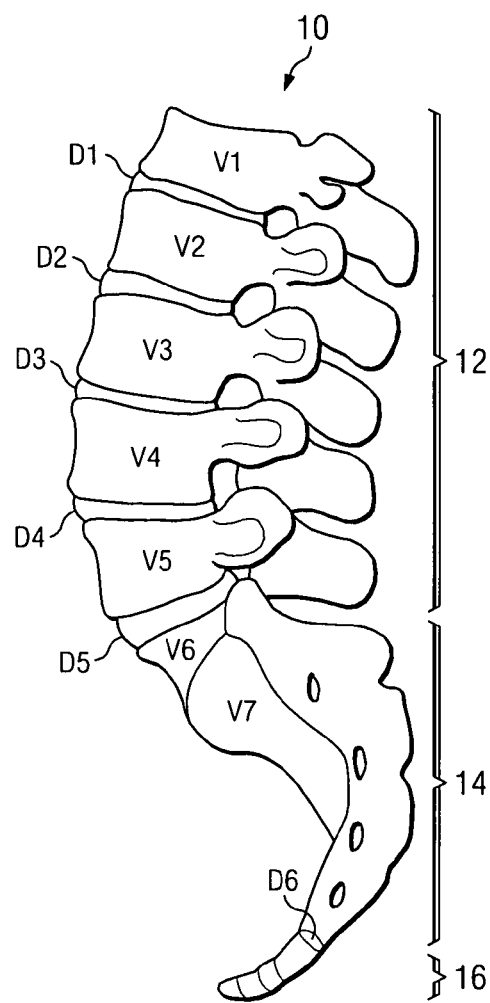
FIG. 1 is a side elevational view of an adult human vertebral column.
Figure 2:
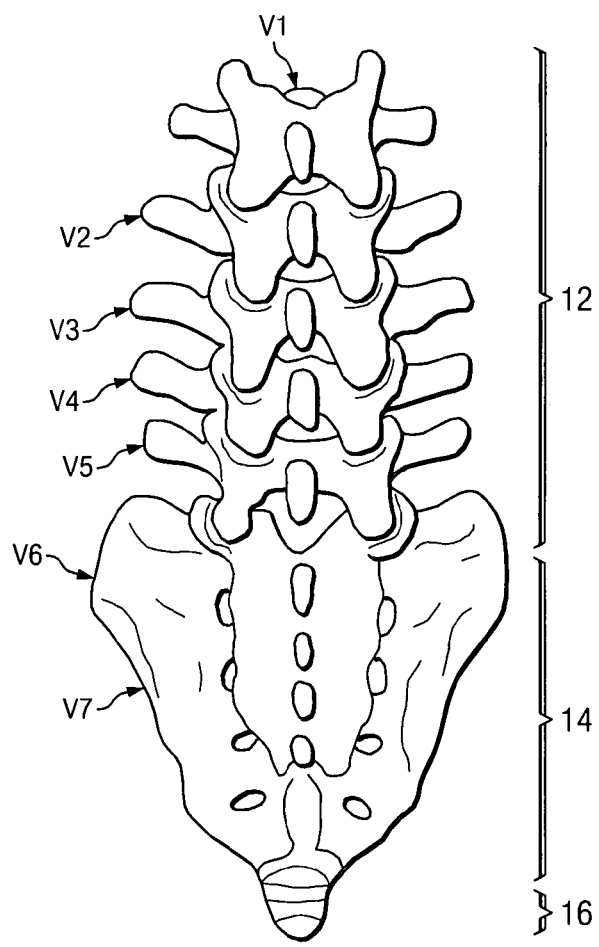
FIG. 2 is a posterior elevational view of the column of FIG. 1.

With reference to FIGS. 1 and 2, the reference numeral 10 refers, in general, to a human vertebral column 10. The lower portion of the vertebral column 10 is shown and includes the lumbar region 12, the sacrum 14, and the coccyx 16. The flexible, soft portion of the vertebral column 10, which includes the thoracic region and the cervical region, is not shown.

The lumbar region 12 of the vertebral column 10 includes five vertebrae V1, V2, V3, V4 and V5 separated by intervertebral discs D1, D2, D3, and D4, with the disc D1 extending between the vertebrae V1 and V2, the disc D2 extending between the vertebrae V2 and V3, the disc D3 extending between the vertebrae V3 and V4, and the disc D4 extending between the vertebrae V4 and V5.

The sacrum 14 includes five fused vertebrae, one of which is a superior vertebrae V6 separated from the vertebrae V5 by a disc D5. The other four fused vertebrae of the sacrum 14 are referred to collectively as V7. A disc D6 separates the sacrum 14 from the coccyx 16, which includes four fused vertebrae (not referenced).

Figure 3:
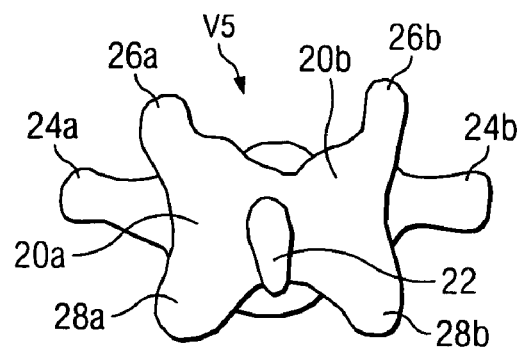
FIG. 3 is an elevational view of one of the vertebrae of the column of FIGS. 1 and 2.

With reference to FIG. 3, the vertebrae V5 includes two laminae 20a and 20b extending to either side (as viewed in FIG. 2) of a spinous process 22 that extends posteriorly from the juncture of the two laminae. Two transverse processes 24a and 24b extend laterally from the laminae 20a and 20b, respectively. Two articular processes 26a and 26b extend superiorly from the laminae 20a and 20b respectively, and two articular processes 28a and 28b extend inferiorly from the laminae 20a and 20b, respectively. The inferior articular processes 28a and 28b rest in the superior articular process of the vertebra V2 to form a facet joint. Since the vertebrae V1-V4 are similar to the vertebrae V5, and since the vertebrae V6 and V7 are not involved in the present invention, they will not be described in detail.

It will be assumed that, for one or more of the reasons set forth above, the vertebrae V4 and V5 are not being adequately supported by the disc D4, and that it is therefore necessary to provide supplemental support and stabilization of these vertebrae. To this end, and referring to FIGS. 4A and 4B, a device according to an embodiment of the invention is shown, in general, by the reference numeral 40 and, for the purposes of example, is shown inserted between the spinous processes 22 of the vertebrae V4 and V5.

The device 40 consists of an enclosed frame 42 formed by four rod-like members 42a-42d. The members 42a and 42b are generally V-shaped and extend opposite one another and the members 42c and 42d are generally V-shaped and extend opposite one another. The member 42a extends between the corresponding ends of the members 42c and 42d, and the member 42b extends between the other ends of the members 42c and 42d. Preferably, the corresponding ends of the members 42a-42d are formed integrally and a notch is formed between their respective ends to permit slight pivotal movement between the members.

Each member 42a-42d is generally V-shaped, with a notch being formed at the apex of the V to permit pivotal movement. As a result of their V-shaped configuration, each member 42a and 42b defines a saddle for receiving a process 22.

Figure 8A:
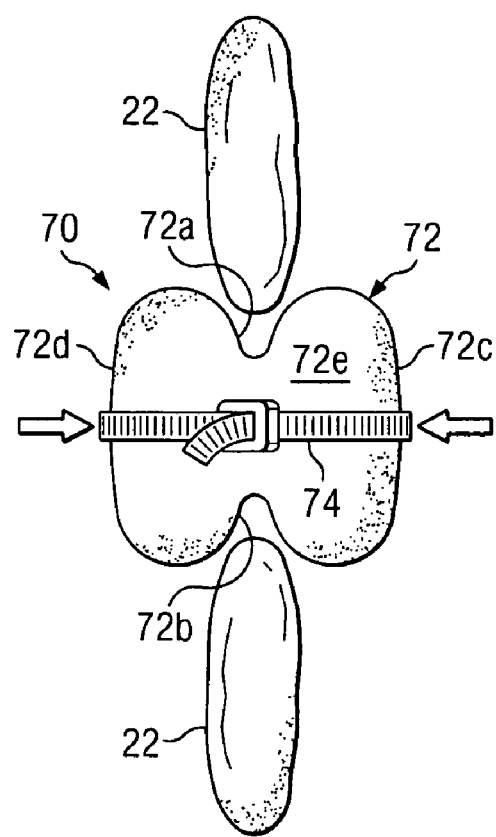
FIGS. 8A and 8B are views similar to those of FIGS. 4A and 4B respectively, but depicting an alternate embodiment.

A retaining member, in the form of a cable tie, or an adjustable strap, 44 extends around the frame 42 and is oriented in the above-mentioned horizontal plane, i.e., in a direction transverse to the axis of the vertebral column 10 (FIGS. 1 and 2). In FIG. 8A, the tie 74 is relatively loose around the members 42c and 42d, and, when tightened, linear forces are applied to the members in the directions shown by the arrows in FIG. 4A as will be described in detail. It is understood that the linear forces exerted by the tie 74 can be adjusted in small increments in the same manner as a conventional cable tie, or by any other appropriate retaining device (not shown).

Figure 4A:
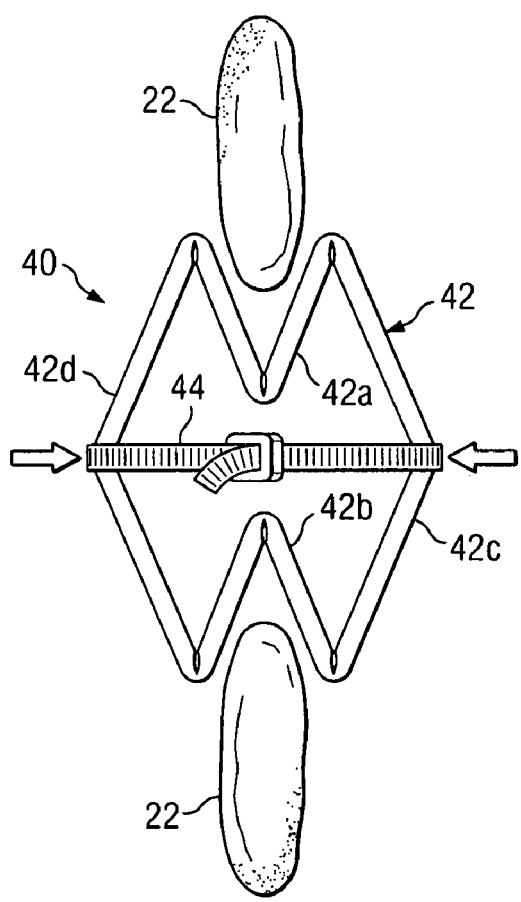
FIG. 4A is a plan view of a device for insertion in the column of FIGS. 1-3.
Figure 5A:
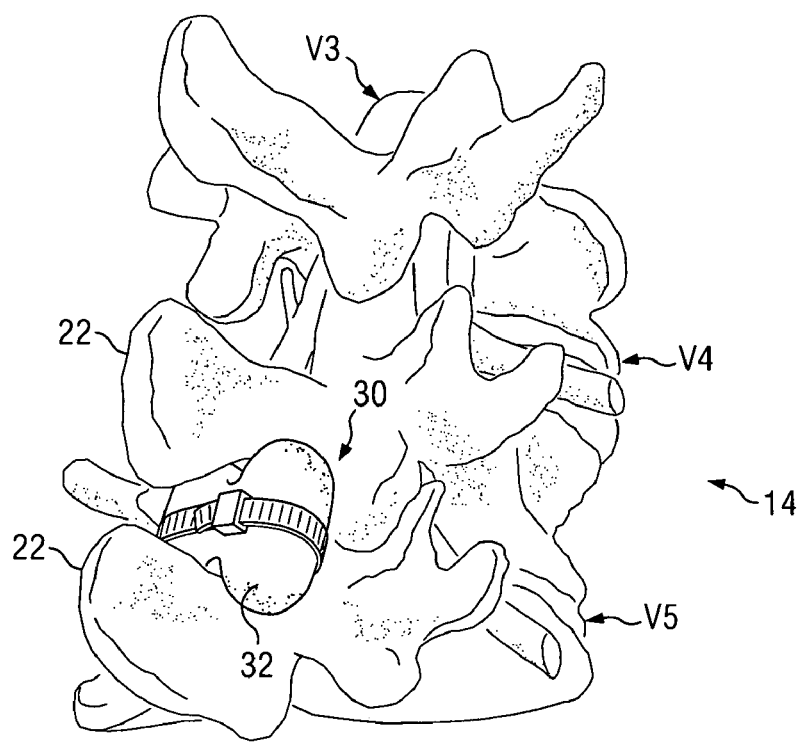
FIG. 5A is an enlarged, partial, isometric view of a portion of the column of FIGS. 1 and 2, including the lower three vertebrae of the column, with the device of FIG. 4A inserted between two adjacent vertebrae.

The device 40 is initially inserted between the processes 22 with the tie 74 loosely fitting around the frame 42 as shown in FIGS. 4A and 5A. In this position the device 40 easily fits between the processes 22, and the processes generally extend in the above-mentioned saddles in a relatively loose arrangement, i.e., they are not pressed against the device with any appreciable force. The surgeon then tightens the tie 44 around the members 42c and 42d as needed to apply an inwardly-directed linear, compressive force to the frame 42 in a plane transverse to the axis of the frame 42, i.e., in the directions shown by the arrows in FIG. 4A.

Figure 4B:
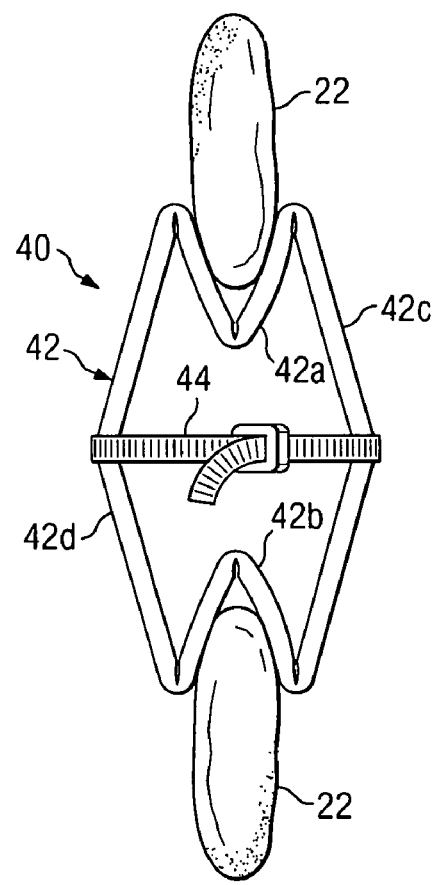
FIG. 4B is a view similar to that of FIG. 4A but depicting the device of FIG. 4A in an expanded condition.
Figure 5B:
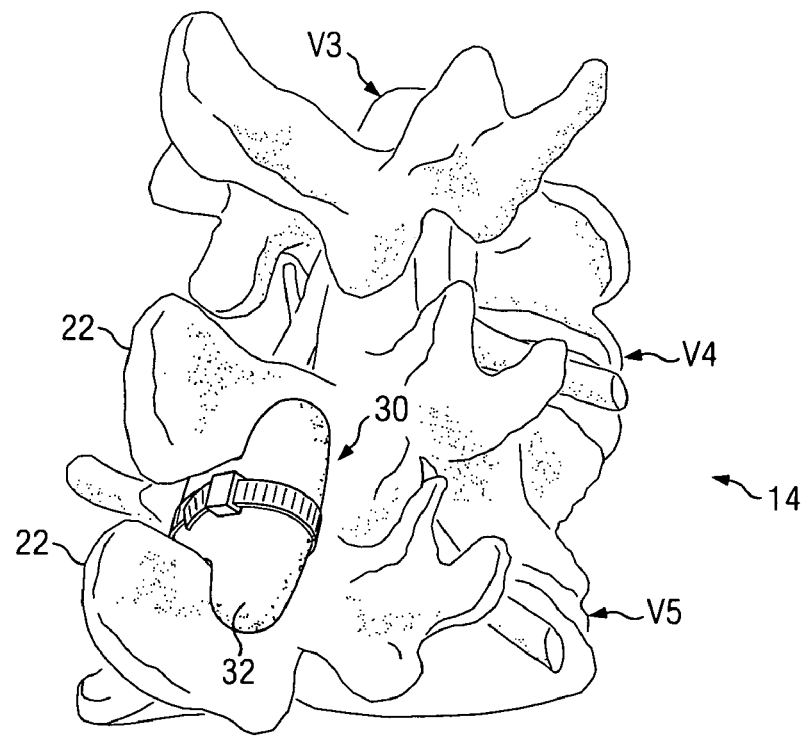
FIG. 5B is a view similar to that of FIG. 4A, but depicting the inserted device of FIG. 5A in its expanded condition of FIG. 4B.

This causes an articulation, or pivotal movement, of the members 42a-42d about the notches discussed above, and the frame 42 is deformed to the position of FIG. 4B. This selective deformation causes the dimension of the frame 42 in a plane transverse to the axis of the vertebral column 10, i.e., a horizontal plane as viewed in the drawings, to be decreased, while its dimension in the plane of the latter column, i.e., a vertical plane, is increased. Thus, the surfaces of the members 42a and 42b defining the saddles press against the process 22 with sufficient force to lock, or retain, the device 40 in the inserted position which is similar to the inserted position of the device 40 shown in FIG. 5B.

The presence of the device 40 prevents the collapse of the intervertebral space between the adjacent vertebrae and thus stabilizes the vertebral column 10. The flexible nature of the device 40 does not cause any damage to the processes 22 and absorbs shock that contributes to the dynamic stabilization of the vertebral column 10.

It can be appreciated that the tie 44 is strong enough to apply the force in the manner described above and to overcome the resistance of the frame 42 to cause the above movement. Therefore, after the device 40 has been implanted in accordance with the above, it will stretch in response to movement of the anatomical structures, such as the processes in the above example, towards each other in response to certain movements of the patient, such as when he or she bends over. In this case, the device 40 can move back from its position shown in FIGS. 4B and 5B towards the position of FIGS. 4A and 5A. Then, after the above movement on part of the patient, the tie 44, and therefore the frame 42, would move back to their normal position of FIGS. 4B and 5B. Alternately, the tie 44 can be relatively rigid (as opposed to stretchable) and the frame members 42a-42d can be stretchable so as to move in response to the above movement of the anatomical structures.

Is also understood the device 40 does not necessarily have to function as an implant as described in the example above, but rather can be used in other different procedures. For example, it can be inserted between the structures, and vertically expanded to an extent that it engages and distracts, or moves, the structures in a direction away from each other, to permit another device, such as a prosthesis, to be implanted between the structures or in an area near the structures. According to another example, the device 40 can be inserted between the structures and vertically expanded to an extent that it engages and distracts the structures to permit another surgical procedure to be performed in the space formed by the distraction. In each of these examples the device 40 would be released and removed after the procedure is completed.

Figure 6A:
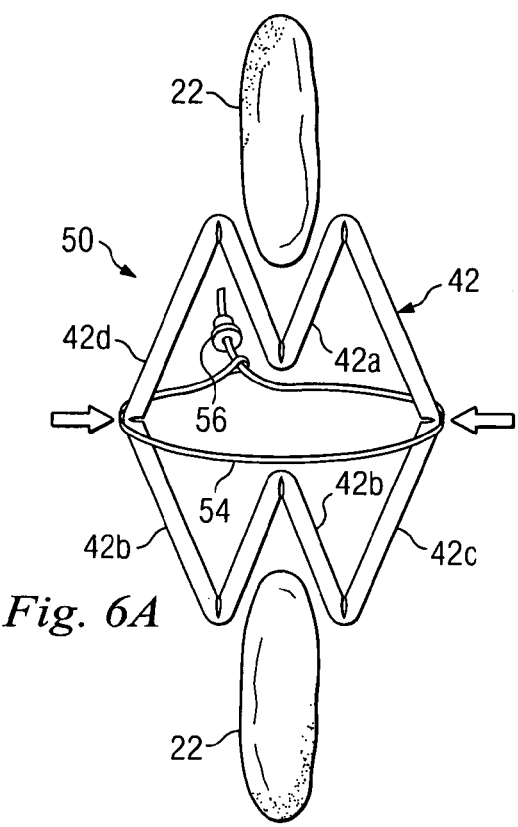
FIGS. 6A and 6B are views similar to those of FIGS. 4A and 4B respectively, but depicting an alternate embodiment.
Figure 6B:
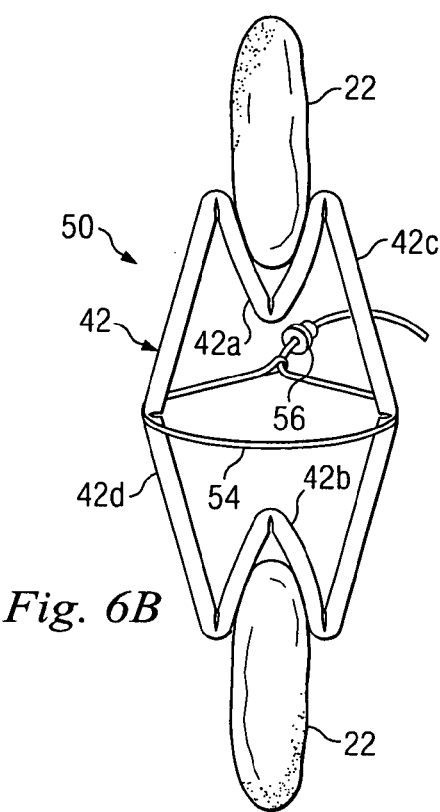

With the exception noted below, the embodiment of FIGS. 6A and 6B is identical to that of FIGS. 4A and 4B and includes components of the latter embodiment, which components are given the same reference numerals.

According to the embodiment of FIGS. 6A and 6B, a device 50 is provided that is identical to the device 40 of the embodiment of FIGS. 4A and 4B, with the exception that the tie 74 of the latter embodiment is replaced by a cable 54 that extends over and around the members 42c and 42d of the frame 42. The end portions of the cable 54 extend through a retaining device 56 to enable the cable to be tightened as necessary to apply linear compressive forces to the frame as shown by the arrows in FIG. 6A, and held in this tightened position.

The device 50 is initially inserted between the processes 22 with the cable 54 loosely fitting around the member 42 as shown in FIG. 6A. In this position, the device 50 easily fits between the processes 22, and the processes generally extend in the saddles defined by the members 42a and 42b in a relatively loose arrangement, i.e., they are not pressed against the device with any appreciable force. The surgeon then tightens the cable 54 to cause an articulation, or pivotal movement, of the members 42a-42d about the notches discussed above in the directions shown by the arrows in FIG. 7A, and the frame 42 is deformed to the position of FIG. 7B.

This selective deformation causes the dimension of the frame 42 in a plane transverse to the axis of the vertebral column 10 to be decreased, while its dimension in the plane of the latter column is increased. Thus, the surfaces of the members 42a and 42b defining the saddles press against the processes 22 with sufficient force to lock or retain the device 50 in the inserted position which is similar to the inserted position of the device 40 shown in FIG. 5B.

The presence of the device 50 prevents the collapse of the intervertebral space between the adjacent vertebrae and thus stabilizes the vertebral column 10. The flexible nature of the device 50 does not cause any damage to the processes 22 and absorbs shock that contributes to the dynamic stabilization of the vertebral column 10.

It can be appreciated that the cable 54 is strong enough to apply the force in the manner described above and to overcome the resistance of the frame 42 to cause the above movement. However, the cable 54 can also have some stretchability, not unlike that of a strong rubber band. Therefore, after the device 50 has been implanted in accordance with the above, it will stretch in response to movement of the anatomical structures, such as the processes in the above example, towards each other in response to certain movements of the patient, such as when he or she bends over. In this case, the device 50 can move back from its position shown in FIG. 6B towards the position of FIG. 6A. Then, after the above movement on part of the patient, the cable 54, and therefore the frame 42, would move back to their normal position of FIG. 6B. Alternately, the cable 54 can be relatively rigid (as opposed to stretchable) and the frame members 42a-42d can be stretchable so as to move in response to the above movement of the anatomical structures.

It is also understood the device 50 does not necessarily have to function as an implant as described in the example above, but rather can be used in other different procedures. For example, it can be inserted between the structures, and vertically expanded to an extent that it engages and distracts, or moves the structures in a direction away from each other, to permit another device, such as a prosthesis, to be implanted between the structures or in an area near the structures. According to another example, the device 50 can be inserted between the structures and vertically expanded to an extent that it engages and distracts the structures to permit another surgical procedure to be performed in the space formed by the distraction. In each of these examples the device 40 would be released and removed after the procedure is completed.

Figure 7A:
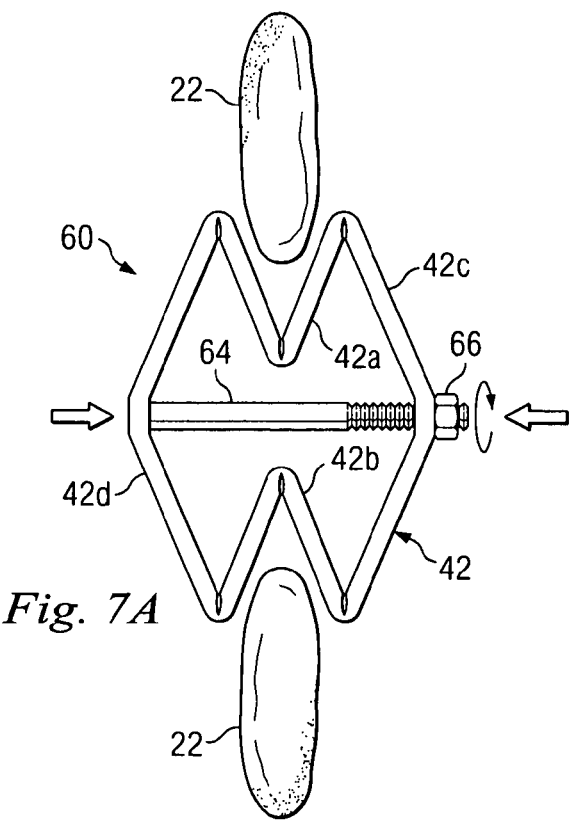
FIGS. 7A and 7B are views similar to those of FIGS. 4A and 4B respectively, but depicting an alternate embodiment.
Figure 7B:
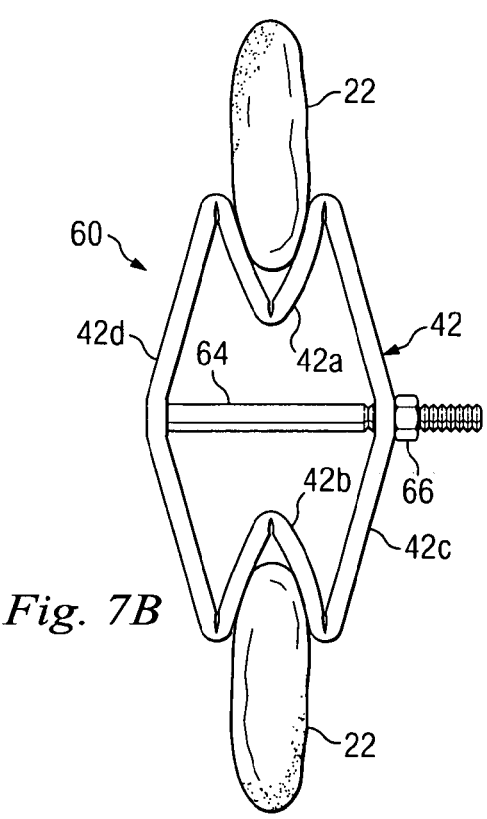

The embodiment of FIGS. 7A and 7B is identical to that of FIGS. 4A and 4B and includes components of the latter embodiment, which components are given the same reference numerals.

According to the embodiment of FIGS. 7A and 7B, a device 60 is provided that is identical to the device 50 of the embodiment of FIGS. 6A and 6B, with the exception that the tie 54 of the latter embodiment is replaced by a bolt 64 and a nut 66. The bolt 64 extends from the member 42d and through the member 42c, and the nut 66 extends outside the frame 42 and is threaded on the threaded end portion of the bolt. Thus, when torque is applied to the nut 66 to tighten it over the bolt 64, an inwardly-directed linear force is applied to the frame 42 in the directions shown by the arrows in FIG. 7A, i.e., in a plane transverse to the axis of the frame 42.

The device 60 is initially inserted between the processes 22 in the position shown in FIG. 8A, with the bolt 64 and the nut 66 exerting little, or no force on the frame 42. In this position the device 60 easily fits between the processes 22 and the processes generally extend in the saddles formed by the frame members 42a and 42b in a relatively loose arrangement, i.e., they are not pressed against the member with any appreciable force.

The surgeon then tightens the nut 66 on the bolt 64, creating a linear compressive force in the directions shown by the arrows in FIG. 7A, sufficient to cause an articulation, or pivotal movement, of the members 42a-42d about the notches discussed above. This selective movement causes the dimension of the frame 42 in a plane transverse to the axis of the vertebral column 10 to be decreased, while its dimension in the plane of the latter column is increased. Thus, the surfaces of the members 42a and 42b defining the above-mentioned saddles press against the processes 22 with sufficient force to lock or retain the device 60 in the position of FIG. 7B which is similar to the inserted position of the device 50 shown in FIG. 5B.

The presence of the device 60 prevents the collapse of the intervertebral space between the adjacent vertebrae and thus stabilizes the vertebral column 10. The flexible nature of the device 60 does not cause any damage to the processes 22 and absorbs shock that contributes to the dynamic stabilization of the vertebral column 10.

It is understood that the frame members 42a-42d can also have some stretchability, as discussed above, so as to permit movement of the anatomical structures, such as the processes in the above example, towards each other in response to certain movements of the patient, such as when he or she bends over. Therefore, after the device 60 has been implanted in accordance with the above, the frame 42 will stretch in response to the load caused by the above movement of the anatomical structures, so that the device can move somewhat from its position shown in FIG. 7B. After the above movement, the frame 42, would move back to its normal position of FIG. 7B.

It is also understood the device 60 does not necessarily have to function as an implant as described in the example above, but rather can be used in other different procedures. For example, it can be inserted between the structures, and vertically expanded to an extent that it engages and distracts, or moves the structures in a direction away from each other, to permit another device, such as a prosthesis, to be implanted between the structures or in an area near the structures. According to another example, the device 60 can be inserted between the structures and vertically expanded to an extent that it engages and distracts the structures to permit another surgical procedure to be performed in the space formed by the distraction. In each of these examples the device 40 would be released and removed after the procedure is completed.

Figure 8B:
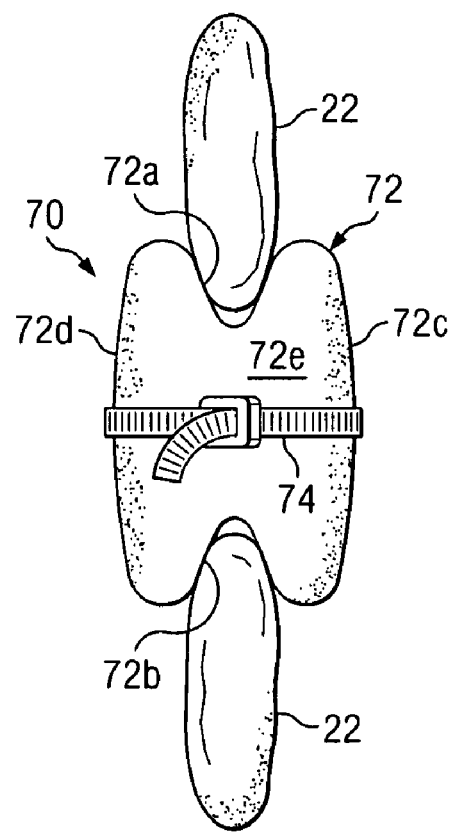

Referring to FIGS. 8A and 8B, an intervertebral disc prosthetic device according to an embodiment of the invention is shown, in general, by the reference numeral 70 and is also designed to be inserted between two anatomical structures, such as the spinous processes 22 of the vertebrae V4 and V5. The device 70 consists of a member 72 having a generally rectangular shape with two end walls 72a and 72b, two side walls 72c and 72d, an upper wall 72e and a lower wall (not shown). The member is fabricated from a material that is characterized by the following.

The side walls 72c and 72d are relatively stiff so as to resist any deformation when a load is applied to the walls, as will be described. The two end walls 72a and 72b are relatively flexible so that they can expand in a manner to be described. The upper wall 72e and the opposite lower wall (not shown) are adapted to contract in a horizontal plane, as viewed in the drawings in the direction indicated by the arrows in FIG. 8A, but are adapted to resist any expansion and contraction in a vertical plane extending perpendicular to the latter horizontal plane. This can be achieved in many ways, such as by adding relatively strong fibers in the material of the member 72 and orienting the fibers in a manner to permit the above contraction and resistance, or by forming the upper wall 72e and the lower wall with vertically extending bellows.

A retaining member, in the form of a cable tie, or an adjustable strap, 74 extends around the member 72 and is oriented in the above-mentioned horizontal plane, i.e., in a direction transverse to the axis of the vertebral column 10 (FIGS. 1 and 2). In FIG. 8A, the tie 74 is relatively loose around the frame 42, and, when tightened, a radial force is applied to the member in the direction shown by the arrows in FIG. 4A to move the member 72 to a vertically expanded position, such as the one shown in FIG. 8B. It is understood that the radial force exerted by the tie 74 can be adjusted in small increments in the same manner as a conventional cable tie, or by any other appropriate retaining device (not shown).

Thus, when the tie 74 is tightened around the member 72, the relatively stiff walls 74c and 74d, the relatively flexible walls 72a and 72b, the wall 72e and the lower wall (not shown) opposite the wall 72c causes the member to expand in a vertical plane and contract in a horizontal place, as viewed in the drawings, as it moves from its position of FIG. 8A to the position of FIG. 8B. Thus, the member 72 responds in a manner similar to that of the frame 42 in the previous embodiments as it moves to the position of FIG. 8B, in which it prevents the collapse of the intervertebral space between the adjacent vertebrae and thus stabilizes the vertebral column 10. The flexible nature of the device 70 absorbs shock which contributes to the dynamic stabilization of the vertebral column 10.

It can be appreciated that the tie 74 is strong enough to apply the force in the manner described above and to overcome the resistance of the member 42 to cause the above movement. However, the tie 74 can also have some stretchability, not unlike that of a strong rubber band. Therefore, after the device 70 has been implanted in accordance with the above, it will stretch in response to movement of the anatomical structures, such as the processes in the above example, towards each other in response to certain movements of the patient, such as when he or she bends over. In this case, the device 70 can move back from its position shown in FIG. 8B towards the position of FIG. 8A. Then, after the above movement on part of the patient, the tie 74, and therefore the member 72, would move back to their normal position of FIG. 8B. Alternately, the tie 74 can be relatively rigid (as opposed to stretchable) and the members 72 can be stretchable so as to move in response to the above movement of the anatomical structures.

Is also understood the device 70 does not necessarily have to function as an implant as described in the example above, but rather can be used in other different procedures. For example, it can be inserted between the structures, and vertically expanded to an extent that it engages and distracts, or moves the structures in a direction away from each other, to permit another device, such as a prosthesis, to be implanted between the structures or in an area near the structures. According to another example, the device 70 can be inserted between the structures and vertically expanded to an extent that it engages and distracts the structures to permit another surgical procedure to be performed in the space formed by the distraction. In each of these examples the device 40 would be released and removed after the procedure is completed.

VARIATIONS

It is understood that variations may be made in the foregoing without departing from the invention and examples of some variations are as follows:

(1) The insertions of the devices 40, 50, 60 and 70 between the spinous processes, as disclosed above, was disclosed above only for the purpose of example, and it is understood that the devices can be used in connection with other anatomical structures.

(2) The frame in one or more of the above embodiments can be rigid and standard hinges can be provided in place of the notches described above to permit the articulating movement.

(3) The devices 40, 50, 60 and 70 can be inserted between two vertebrae following a corpectomy in which at least one vertebrae is removed.

(4) Other techniques, such as a ratchet arrangement or a rack and pinion arrangement can be used for applying the forces to the frame 42 and the member 72.

(5) The frame 42 and the member 72 can be oriented perpendicular to the spinous process rather than parallel as shown in the drawings.

(6) Another member of a different shape can replace the frame 42 or the member 72.

(7) The particular location of the devices 40, 50, 60 and 70 in the human anatomy can be varied.

(8) Any spatial references made above, such as "under", "over", "between", "upper", "lower", "top", "bottom", etc. are for the purpose of illustration only and do not limit the specific orientation or location of the structure described above.

The preceding specific embodiments are illustrative of the practice of the invention. It is to be understood, therefore, that other expedients known to those skilled in the art or disclosed herein, may be employed without departing from the invention or the scope of the appended claims, as detailed above. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw are equivalent structures.

What is claimed is:

1. An interspinous implant for insertion between upper and lower spinous processes, comprising:
    a spacer having first and second protrusions extending substantially upwardly and third and fourth protrusions extending substantially downwardly, the spacer further comprising posterior and anterior surfaces;
    the first and second protrusions forming an upwardly facing concave saddle and the third and fourth protrusions forming a downwardly facing concave saddle, wherein the saddles extend to the posterior and anterior surfaces;
    a strap extending circumferentially around the spacer such that the strap extends around the posterior and anterior surfaces and extends substantially transverse to the first, second, third and fourth protrusions;
    the strap coupled to the spacer such that tightening the strap causes the upwardly and downwardly facing concave saddles to move away from each other;
    wherein the spacer is configured such that, when the implant is inserted between the upper and lower spinous processes such that the saddles receive the upper and lower spinous processes, the posterior and anterior surfaces extend through a sagittal plane defined by the upper and lower spinous processes.

2. The implant of claim 1 wherein the implant includes a pair of opposing lateral convex sides, each convex side having a hinge disposed between upper and lower sections.

3. The implant of claim 2 wherein the convex sides are configured to articulate in response to tightening of the strap.

4. A method of implanting an interspinous implant, comprising:
    inserting the interspinous implant recited in claim 1 between upper and lower spinous processes such that the upwardly facing concave saddle and the downwardly facing concave saddle receive the upper and lower spinous processes respectively; and
    tightening the strap.

5. An interspinous implant for insertion between upper and lower spinous processes, comprising:
    an upwardly facing concave saddle and a downwardly facing concave saddle, the saddles configured to receive the upper and lower spinous process respectively;
    first and second generally oppositely facing convex sides operatively coupled to the saddles;
    a strap operatively coupled to the upwardly and downwardly facing saddles such that tightening the strap causes both the first and second convex sides to change shape and the upwardly and downwardly facing concave saddles move away from each other;
    wherein a portion of the strap extends along an exterior circumference of the spacer disposed between the upwardly and downwardly facing saddles;
    wherein the implant is configured such that, when the implant is inserted between the upper and lower spinous processes, the portion of the strap extends through a sagittal plane defined by the spinous processes.

6. The implant of claim 5 wherein the saddles and the convex sides form a portion of an articulating frame; wherein the first and second convex sides are each pivotally coupled to both saddles.

7. The implant of claim 6 wherein each of the convex sides includes a hinge, and wherein the convex sides are configured to articulate at least at the hinges in response to tightening of the strap.

8. A method of implanting an interspinous implant, comprising:
    inserting the interspinous implant recited in claim 5 between upper and lower spinous processes such that the upwardly facing concave saddle and the downwardly facing concave saddle receive the upper and lower spinous processes respectively; and
    tightening the strap.

* * * * *